United States Patent
Leon et al.

(10) Patent No.: US 7,074,210 B2
(45) Date of Patent: Jul. 11, 2006

(54) UNIVERSAL PROTECTOR CAP WITH AUTO-DISABLE FEATURES FOR NEEDLE-FREE INJECTORS

(75) Inventors: Nathaniel J. Leon, Shawnee, KS (US); Victor T. Rogatchev, Voronezh (RU); Michael Mathews, Lees Summit, MO (US)

(73) Assignee: Felton International, Inc., Lenexa, KS (US)

( * ) Notice: Subject to any disclaimer, the term of this patent is extended or adjusted under 35 U.S.C. 154(b) by 165 days.

(21) Appl. No.: 10/269,548

(22) Filed: Oct. 11, 2002

(65) Prior Publication Data

US 2003/0088214 A1 May 8, 2003

Related U.S. Application Data

(63) Continuation-in-part of application No. 09/685,499, filed on Oct. 10, 2000, now Pat. No. 6,802,826.

(60) Provisional application No. 60/329,081, filed on Oct. 12, 2001.

(51) Int. Cl.
*A61M 5/32* (2006.01)
*A61M 5/30* (2006.01)
*A61M 37/00* (2006.01)
*A61M 5/178* (2006.01)
*A61M 25/00* (2006.01)

(52) U.S. Cl. .................. 604/192; 604/68; 604/69; 604/70; 604/71; 604/72; 604/46; 604/47; 604/131; 604/218; 604/213; 604/215; 604/268

(58) Field of Classification Search ............... 604/192, 604/68, 69, 70, 71, 72, 198, 46, 47, 131, 604/218, 213, 215, 268
See application file for complete search history.

(56) References Cited

U.S. PATENT DOCUMENTS

| | | | | |
|---|---|---|---|---|
| 2,667,874 A | * | 2/1954 | Dickson, Jr. | 604/72 |
| 3,131,692 A | * | 5/1964 | Stanley | 604/68 |
| 3,518,990 A | | 7/1970 | Banker | |
| 3,788,315 A | | 1/1974 | Laurens | |
| 4,124,024 A | | 11/1978 | Schwebel et al. | |
| 4,165,800 A | * | 8/1979 | Doherty et al. | 604/68 |
| 4,386,384 A | * | 5/1983 | Moran | 361/94 |
| 4,396,384 A | * | 8/1983 | Dettbarn et al. | 604/68 |
| 4,578,061 A | * | 3/1986 | Lemelson | 604/170.01 |
| 4,592,742 A | | 6/1986 | Landau | |
| 4,722,729 A | * | 2/1988 | Dettbarn et al. | 604/71 |
| 5,024,656 A | | 6/1991 | Gasaway et al. | |
| 5,080,648 A | * | 1/1992 | D'Antonio | 604/72 |

(Continued)

FOREIGN PATENT DOCUMENTS

FR 2629348 10/1989

(Continued)

OTHER PUBLICATIONS

International Search Report (PCT/US 02/32649) (Including Cited References) (Oct. 11, 2002).

(Continued)

*Primary Examiner*—Henry Bennett
*Assistant Examiner*—Nihir Patel
(74) *Attorney, Agent, or Firm*—Joseph A. Mahoney; Mayer, Brown, Rowe & Maw, LLP

(57) ABSTRACT

Disclosed is a medical device used to prevent the cross-contamination of patients or injectors in which various components placed on the injector minimize or eliminate back splash contamination of the injector.

10 Claims, 6 Drawing Sheets

U.S. PATENT DOCUMENTS

| | | | |
|---|---|---|---|
| 5,190,523 A | 3/1993 | Lindmayer | |
| 5,256,142 A | 10/1993 | Colavecchio | |
| 5,334,144 A * | 8/1994 | Alchas et al. | 604/68 |
| 5,354,286 A | 10/1994 | Mesa et al. | |
| 5,503,627 A | 4/1996 | McKinnon et al. | |
| 5,730,723 A | 3/1998 | Castellano et al. | |
| 5,830,193 A | 11/1998 | Higashikawa | |
| 5,836,911 A | 11/1998 | Marzynski et al. | |
| 6,056,716 A * | 5/2000 | D'Antonio et al. | 604/68 |
| 6,102,896 A * | 8/2000 | Roser | 604/218 |
| 6,132,395 A * | 10/2000 | Landau et al. | 604/68 |
| 6,135,979 A * | 10/2000 | Weston | 604/68 |
| 6,210,359 B1 * | 4/2001 | Patel et al. | 604/68 |
| 6,224,567 B1 * | 5/2001 | Roser | 604/68 |
| 6,264,629 B1 * | 7/2001 | Landau | 604/68 |
| 6,270,473 B1 | 8/2001 | Schwebel | |
| 6,309,371 B1 | 10/2001 | Deboer et al. | |
| 6,344,027 B1 * | 2/2002 | Goll | 604/68 |
| 6,383,168 B1 * | 5/2002 | Landau et al. | 604/268 |
| 6,406,456 B1 | 6/2002 | Slate et al. | |
| 6,471,669 B1 * | 10/2002 | Landau | 604/68 |
| 6,506,177 B1 * | 1/2003 | Landau | 604/68 |
| 6,610,029 B1 * | 8/2003 | Golan | 604/68 |
| 6,620,135 B1 * | 9/2003 | Weston et al. | 604/69 |
| 6,641,554 B1 * | 11/2003 | Landau | 604/68 |
| 6,802,826 B1 * | 10/2004 | Smoliarov et al. | 604/192 |
| 6,979,310 B1 * | 12/2005 | Navelier et al. | 604/70 |
| 2001/0131945 | 10/2001 | Haar et al. | |

FOREIGN PATENT DOCUMENTS

| | | |
|---|---|---|
| FR | 2641190 | 7/1990 |
| RO | 0106078 | 2/1993 |
| RO | 0108150 | 2/1994 |
| RU | 0476876 | 10/1975 |

OTHER PUBLICATIONS

Dimache, et al., A Clinical, Epidemiological and Laboratory Study on Avoiding the Risk of Transmitting Viral Hepatitis During Vaccinations with the Dermojet Protected by an Anticontaminant Disposable Device, *Vaccine*, vol. 15, No. 8, pp 1010-13 (1997).

Jet Gun Injection Transmission: A Clinical, Epidemiological and Laboratory Study on Avoiding the Risk of Transmitting Viral Heptatis During Vaccinations with the Dermojet Protected by an Anticontaminant Disposable Device, *American Journal of Infection Control*, vol. 26, No. 4, pp. 442-5 (Aug. 1998).

* cited by examiner

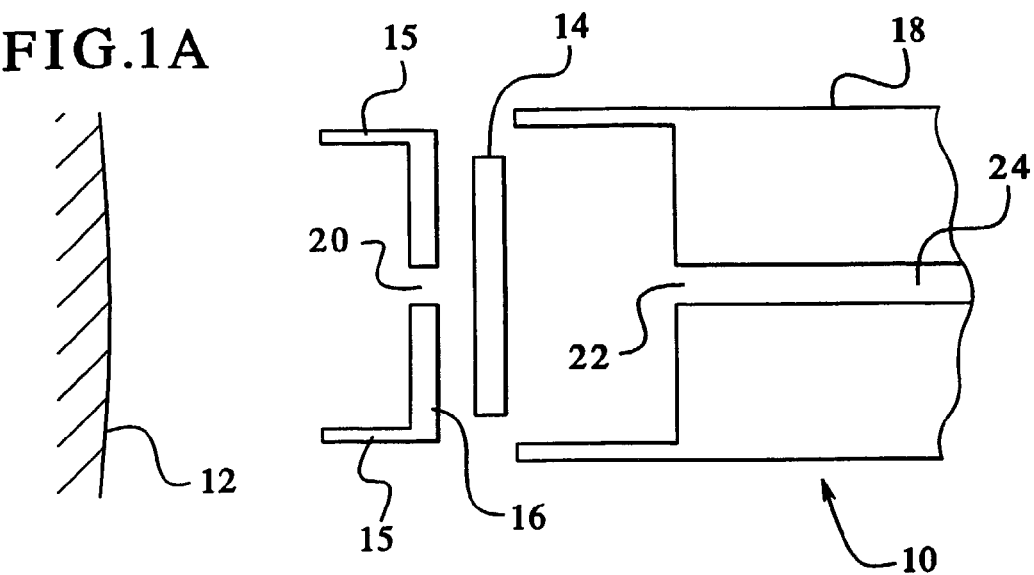
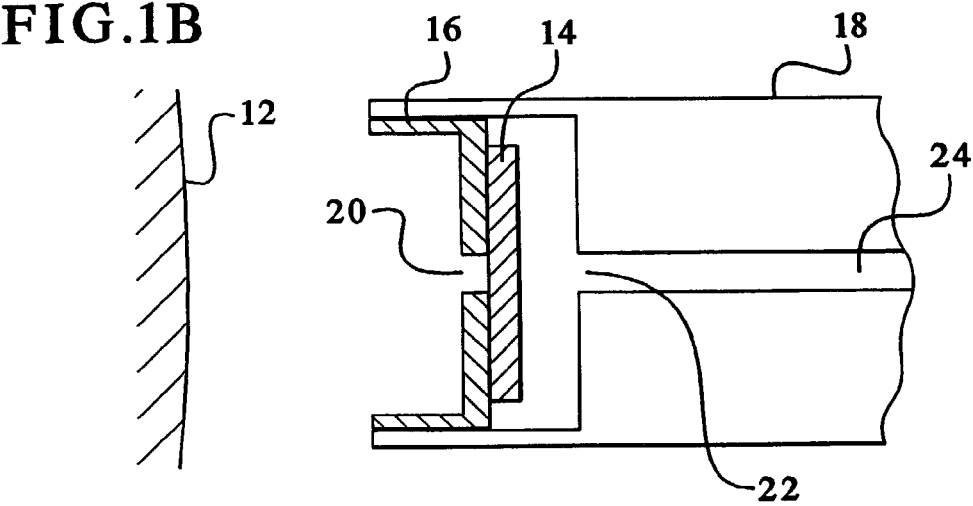
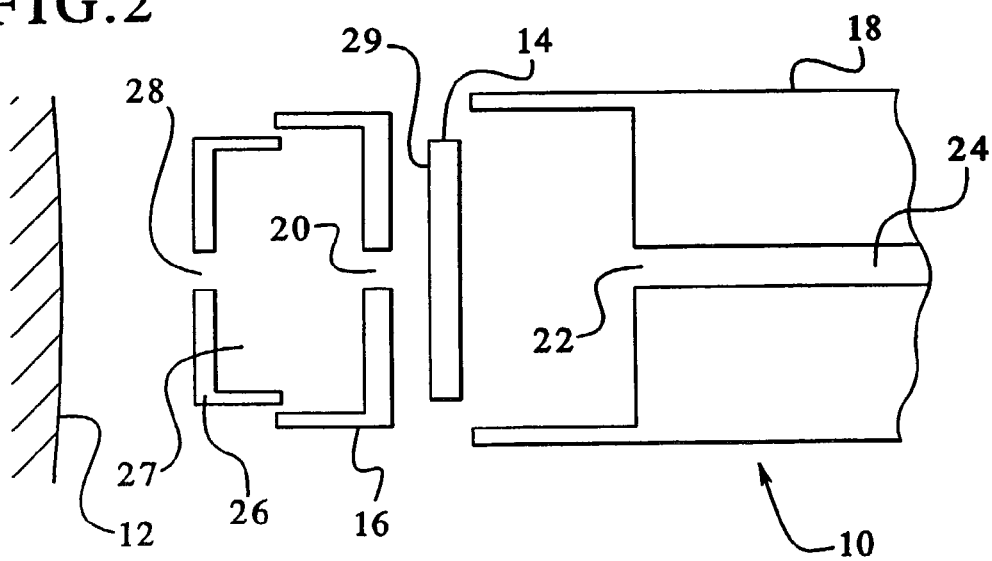

UNIVERSAL PROTECTOR CAP WITH AUTO-DISABLE FEATURES FOR NEEDLE-FREE INJECTORS

CROSS REFERENCE TO RELATED APPLICATIONS

Pursuant to 35 U.S.C. §§ 119(e) and 120, this application is a continuation-in-part application of U.S. application Ser. No. 09/685,499, filed Oct. 10, 2000, now U.S. Pat. No. 6,802,826 which claims priority to Russian Application No. 99121141, filed Oct. 12, 1999 and Russian Application No. 99124268, filed Nov. 23, 1999, and this application claims priority to prior U.S. provisional application No. 60/329,081, filed Oct. 12, 2001, the disclosures of which are incorporated herein by reference.

FIELD OF THE INVENTION

The present invention relates to a protector cap with an auto-disable feature for needle-free drug delivery devices for animal and human health applications.

BACKGROUND OF THE INVENTION

The most effective measure to prevent many diseases among animals and/or humans is the mass immunization with vaccines. Needle-free injectors have been used to accomplish this task. The traditional needle-free injectors comprise the basic design, a housing with an inner power unit, a medication unit, and a nozzle. The power unit pumps the medication into an under-plunger cavity of the medication unit chamber and expels the medication through the nozzle.

With the use of a typical jet injector, there exists the possibility of infection transfer from one subject to another by means of fluids (blood, lymph, medication) reflected from the skin surface during injection ("back splash") that may get on the nozzle and be transferred from one patient to the next. Further, in the injection stage, the contaminated matter can be transferred through the nozzle to inside the injector such as, for example, into the cavity and be transmitted to a new patient through a new cap and nozzle.

Accordingly, there is a need in the art of needle-free injection devices to solve the problem of cross-contamination during mass vaccinations. More particularly, there is a need for a protector designed for the nozzle head of needle-free injectors, which halts "back splash" contamination, and which is low enough in cost to ensure its practical application as a disposable unit even for mass vaccinations.

SUMMARY OF THE INVENTION

The preceding problems are solved and a technical advance is achieved by the present invention. Disclosed is a protector cap for a needle-free injector having an insert and a baffle integrally joined and a disable device located between the insert and the baffle.

The protective cap may be a one-shot cap. One purpose of this device is to prevent the multiple use of a cap. This may be achieved through the removal, replacement, and/or destruction of the cap at the later stage of the injection.

BRIEF DESCRIPTION OF DRAWINGS

FIG. 1A demonstrates an exploded view of a simple embodiment of the present invention.

FIG. 1B demonstrates the simple embodiment in assembled form.

FIG. 2 shows an exploded view of another embodiment of the present invention in which another component is introduced.

DETAILED DESCRIPTION

Figure 3:
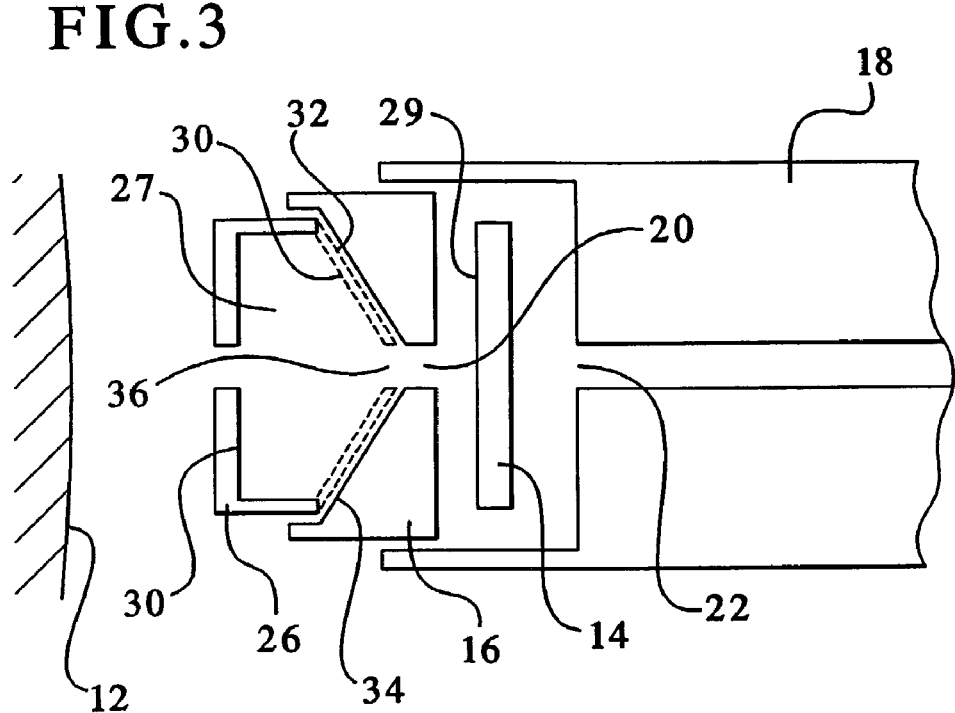
FIG. 3 shows an exploded view of another embodiment of the present invention in which some components are modified.

FIG. 1A demonstrates an exploded view of the present invention. An injector assembly 10 is shown. One purpose of the injector assembly 10 is to provide needless injection of medicaments into the skin 12. As described herein, the injector assembly 10 is provided with a layer, such as protective layer 14. The protective layer 14 generally comprises a material that is adapted to permit the injection of medicaments in one direction, yet minimize or retard the reverse flow. The source of the medicament jet stream is from an injector 18. In this regard, the protective layer 14 can serve as a back splash guard. In this particular, exemplary, and non-limiting embodiment, an optional baffle 16 is provided to facilitate the diminution of back splash.

The baffle 16 may further comprises a baffle orifice 20, which can take any desired shape or size, depending on the intended use. In this regard, the length and cross-section of the baffle orifice 20 will influence how much back splash hits the protective layer 14. It is contemplated in all embodiments that the size of the baffle orifice 20 can be sized to minimize disruption of the medicament jet stream yet maximize the protection afforded by the protective layer 14. If the baffle orifice 20 is too small, the baffle 16 may disrupt the jet stream and thereby reduce the energy of the stream. If too much diminution of the stream energy occurs, then the jet stream will not penetrate the skin 12 in the desired fashion to the desired depth.

Baffle 16 can be sized to accommodate the needed configuration, and may optionally include baffle wings 15 to ensure proper skin stand-off. Of course the length and diameters may vary significantly, but in one example, baffle 16 can be approximately greater than 11 mm in diameter and 5 mm tall. Generally, the diameter of the baffle orifice 20 should be slightly larger than the diameter of the jet stream. Therefore, it does not really matter how large the baffle orifice 20 is so long as it is slightly larger than the jet stream diameter, irrespective of the diameter of the injector orifice 22.

Injector 18 has an injector orifice 22 at the distal end of an injector canal 24. The medication sought to be injected travels through the injector canal 24, exits through the injector orifice 22 and punctures the protective layer 14. The medication jet stream then enters the baffle orifice 20 and impacts the skin 12. The energy of the jet stream is chosen to provide the desired injection, depth, and location. For example, for a deeper injection, a higher energy will be necessary. The medicament jet stream then enters the skin 12 and travels to the desired situs. However, the impact on skin 12 is not without some attendant consequences. One consequence is that surface tissue, fluids, cells, and cellular contents are removed or ablated from the surface of skin 12 and fly about. This back splash of debris can travel back along the jet stream and impact the baffle 16 and protective layer 14. The debris, though, is generally not traveling fast enough to re-puncture the protective layer 14. In this regard, the protective layer 14 retards or minimizes the debris back splash into the injector orifice 22 and the injector 18. One function of the layer 14 is to prevent the contamination of the injector 18. In this regard, the simple concept of the invention is to protect the injector orifice 22 from contamination. Thus, in the event no baffle 16 is used, the injector 18 itself may bear the protective layer 14.

The material chosen for the layer 14 may comprise any material that facilitates a fluid stream puncture in one direction, yet retard the fluid stream puncture in the opposite direction. For example, the layer 14 can comprise a biochemically inert material that is approved for contact with pharmaceuticals, such as but not limited to, at least one of a plastic, rubber, polymer, polyethylene, polytetrafloroethylene, polyurethane, polypropylene, polyolefin, and polysulfone material. In this regard, a material that permits the perforation by the jet stream in one direction but then seals upon itself after the jet stream stops is more desirable. The protective layer or layers are desirably thin, for example greater than 0.001 mm. Preferably and nonexclusively, the thickness can range in the about 0.004 to 0.08 mm range with a further thickness of about 0.2 to 0.5 mm. It should be noted that the thickness chosen is variable. Protective layer 14 may also be textured, woven, braided, or so configured to provide a better adhesion, if necessary, or to provide better attachment, or to prevent or minimize movement. For example, the layer 14 may have grooves of various types. As mentioned, the diameter of the protective layer 14 (if a disc, or the width if a strip) should be slightly larger than the diameter of the jet stream.

As shown in FIG. 1A, the components are in exploded view. In assembly, the baffle 16 can be designed to fit within the injector 18 and sandwich the layer 14 generally between the baffle 16 and injector 18. Desirably, the injector orifice 22 and baffle orifice 20 should line up to minimize any diminution of the stream energy. As with any connection and assembly herein, the baffle 16 can be adapted to provide a friction fit, snap fit, screw fit, or bayonet fit. Any component herein can also be heatsealed to fit.

Protective layer 14 can be also adhered, bonded, or otherwise attached to the injector 18, baffle 16 or to any part as desired.

FIG. 1B demonstrates a simple embodiment of the present invention. As one can see, the protective layer 14 can be generally sandwiched between baffle 16 and the injector 18. The protective layer 14 can be totally sandwiched or partially sandwiched between the components described herein.

As the medication is injected out through injector canal 24 and injector orifice 22, it will penetrate through the layer 14 and through the baffle orifice 20.

It should be noted that in any embodiment of the present invention, the medication need not be liquid. In addition to aqueous solutions, the present invention may employ suspensions, aqueous gels, emulsions, or controlled release injectable medications. One other dosage form includes powder. For example, Powderject Pharmaceuticals, of Oxford, United Kingdom, and/or Powderject Vaccines (Madison, Wisc.) have developed an injector that propels medicine in powder form in the same manner as traditional needle-free injectors. For example, see, U.S. Pat. Nos. 5,733,600; 6,053,889; and 5,899,880; the disclosures of which are expressly and entirely incorporated herein. Since the powder form of drugs take up less than 1% of the volume of drugs in liquid form, adapting the powder injectors to be used in accordance with the present invention is also contemplated.

Generally, but not exclusively, the powder particles of one dose can range in size but are generally 50 microns wide, as compared to a 500 micron wide syringe needle. In other words, powder form vaccines, such as recombinant DNA based vaccines, including Hepatitis B and HIV vaccines, and other medications for treating influenza, tetanus, erectile dysfunction, allergies, pain, cancer, etc., are contemplated. Such powder forms may be admixed with small amounts of sterile water or other physiologically acceptable diluents (e.g., about 1–10%) to form pastes or suspensions. Therefore, adapting the powder injectors to have a protective cap and/or film consistent with the present invention is within the ordinary skill in the art.

FIG. 2 demonstrates another embodiment of the present invention. The injector assembly 10 is shown having a baffle 16 and an insert 26. The insert 26 can be adapted to form an insert reservoir 27. Insert 26 also has an insert distal orifice 28. Insert 26 can be adapted to fit with baffle 16 such that the insert 26 provides an additional benefit of back splash protection, during or after the injection is completed. Insert 26 can be adapted to fit with baffle 16 such that insert 26 helps to properly tension the skin for the injection type (intramuscular, subcutaneous, or intradermal). As shown in this particular, exemplary, and non-limiting embodiment, the protective layer 14 is generally located between, either partially or completely, the baffle 16 and the injector orifice 22. In this configuration, the jet stream will exit the injector orifice 22, penetrate through the layer 14, and exit through the baffle orifice 20 and insert distal orifice 28 to impact the skin 12. The skin debris will back splash against the insert 26 and any debris that flies into the insert distal orifice 28 will likely be stopped by the baffle 16. In the event that debris trajectory permits debris to travel through the baffle orifice 20, the debris will impact the distal surface 29 of layer 14.

In this regard, the injector orifice 22 is protected against contamination. The debris that hits the protective layer distal surface 29 will likely fall into the insert reservoir 27 and collect there. Insert 26 can be adapted to fit into the baffle 16 as needed. One benefit of the insert configuration is the disposability of the unit. As for configuration, the injector orifice 22 can be varying distances away from the skin 12. For example, it can be adjacent the skin 12 (where a baffle or insert is not used and the layer 14 is attached directly to the injector 18), or millimetres away, such as 2–15 mm away. Naturally the distance chosen will reflect on the stream energy. Desirably, the injector orifice 22 distance from the skin 12 is chosen with this in mind. In some configurations, the proximal face of the baffle 16 could be millimetres away from the skin, such as 2–15 mm and desirably 2–7 mm. Insert orifice 28 diameter is also sized accordingly, such as 0.001 mm or greater. In one commercial embodiment, however, the insert 26, baffle 16, and protective layer 14 can be discarded as a unit upon contamination.

FIG. 3 represents another embodiment of the present invention. Shown are the baffle 16, insert 26, protective layer 14, and injector 18. In this configuration the baffle 16 is adapted to provide a greater surface area exposed to potential back splash. The insert 26 is also adapted to minimize back splash contamination. For example, insert 26 has an insert inner surface 30 and an insert outer surface 32. As shown in dotted lines, the insert 26 can be configured to form "wings" in which the insert 26 will cooperate with the baffle 16. Baffle 16 has a baffle inner surface 34 that cooperates with the insert 26. As shown in this embodiment, the insert outer surface 32 is in cooperation with the baffle inner surface 34. The wings of the insert 26 come into proximity of each other to form an insert proximal orifice 36. In this embodiment, any back splash of skin debris entering the insert distal orifice 28 will likely hit the insert inner surface 30, or the baffle inner surface 34, or the distal surface 29 of protective layer 14. In the event insert 26 is configured to not have wings, any debris can still hit the insert inner surface 30, the baffle inner surface 34, or the distal surface 29 of protective layer 14.

Figure 4:
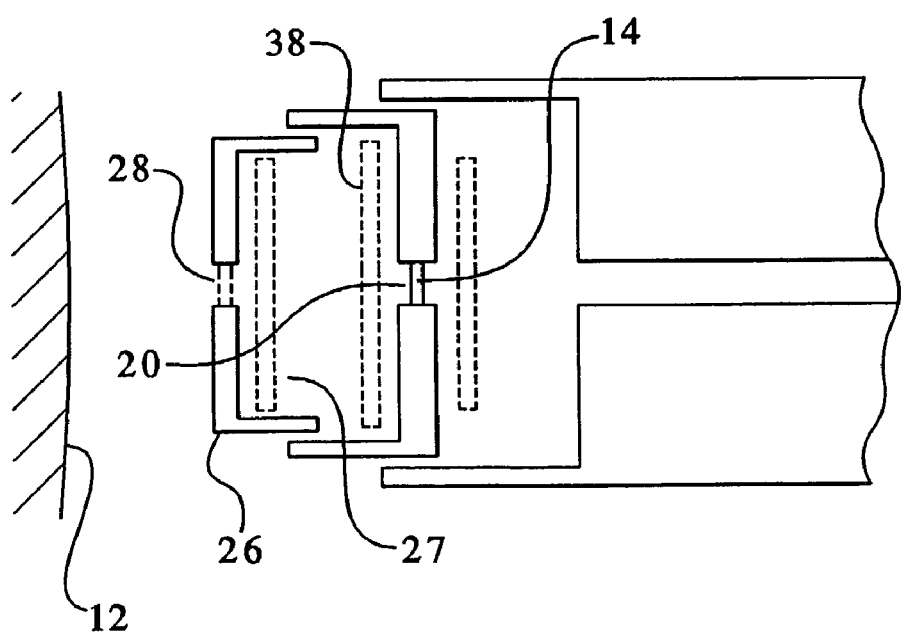
FIG. 4 shows other embodiments of the present invention in which a protective layer is shown at various positions.

FIG. 4 demonstrates yet another embodiment of the invention. Shown is a plurality of protective layers 14 shown in phantom 38. In this exemplary and non-limiting embodiment, the protective layer 14 is shown covering the baffle orifice 20. The protective layer 14 can be integrally formed with the baffle 16 or can be separately affixed to the baffle 16. In this embodiment, the removal of the baffle 16 facilitates disposability.

Also shown is that multiple protective layers 14 are present. Protective layers 14 can be generally found proximal the skin, coincident with the insert distal orifice 28, proximal to the insert distal orifice 28, distal to the baffle 16, distal to the baffle orifice 20, coincident with the baffle orifice 20, or proximal to the baffle orifice 20. The number of protective layers can be chosen to maximize the jet stream energy for puncture purposes, but diminish back splash contamination potential. Also shown in FIG. 4 is the assembly in which the insert 26 and baffle 16 are within the injector assembly 18. Where multiple layers are used, the layers can be attached using bonding, heatsealing, or sandwiching the layers.

Figure 7A:
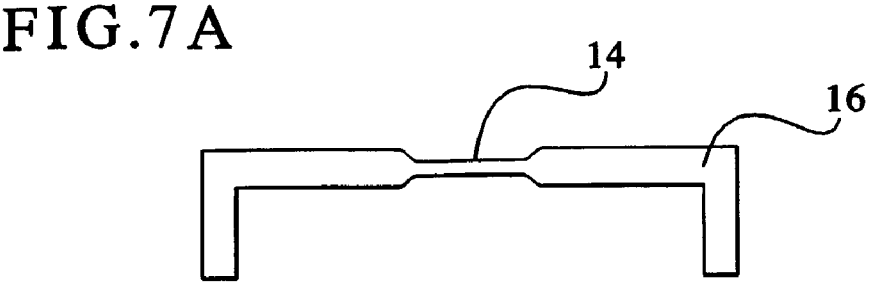
FIGS. 7A–D depict several different embodiments of the protective layer of the present invention.
Figure 7B:
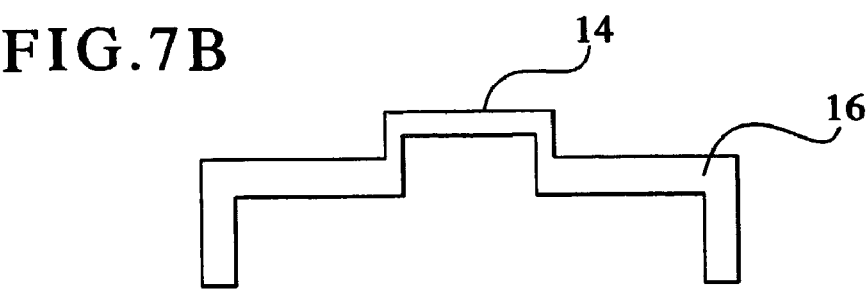
Figure 7C:
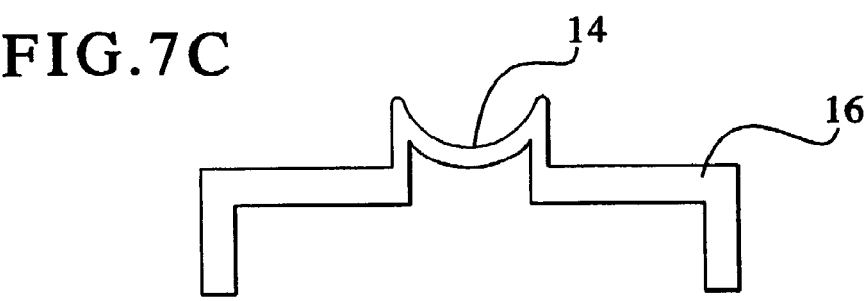
Figure 7D:
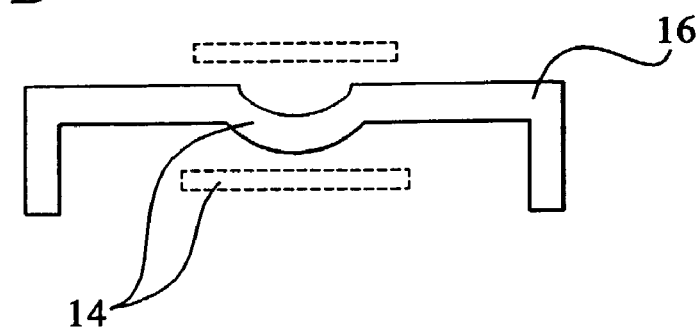

As seen in FIGS. 7A–D, it should be noted that in any embodiment herein, the protective layer 14 or film need not be a separate piece. Rather it may be integrally formed with a component, such as a septum. For example, the protective layer 14 may be part of the baffle 16 in which that area that will be punctured by the jet stream is adapted to give way during injection. For example, if the baffle 16 is made of plastic, then the area that will serve as the protective layer can be integral with the baffle 16 yet be "ground" down slightly to make it thinner or more easily adapted to perforation. In yet another embodiment, the layer 14 may be separately manufactured then adhered in some fashion to a component, such as the baffle 16. In yet another embodiment as shown in FIG. 7D, a plurality of films may also be used (as shown in phantom lines).

Figure 5:
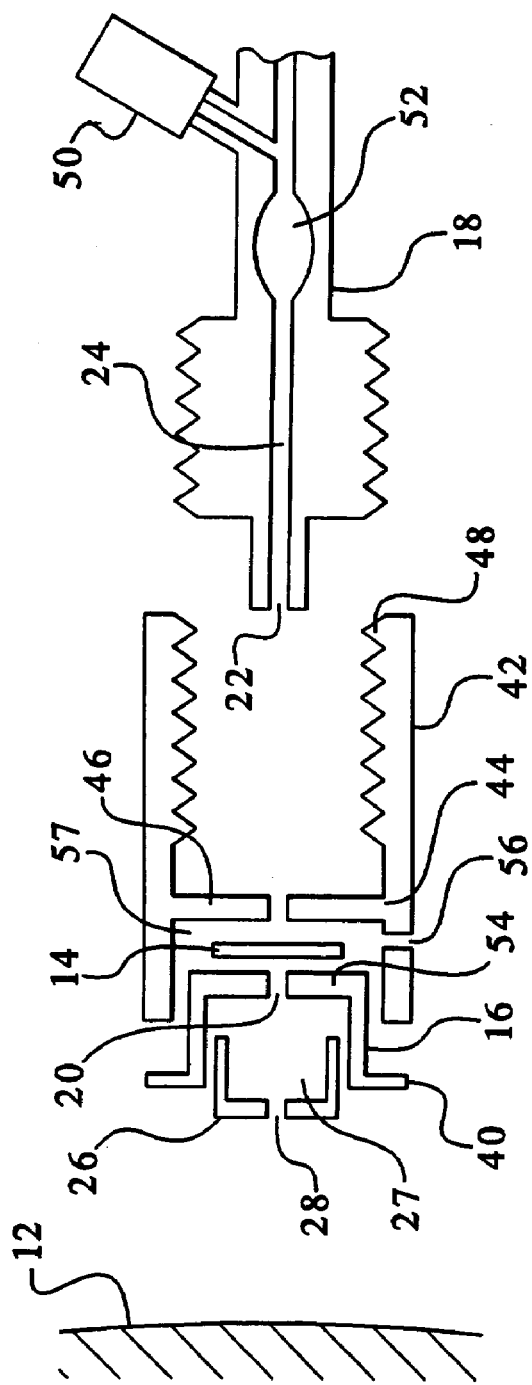
FIG. 5 shows yet another embodiment of the present invention in which an intermediate piece is shown.

FIG. 5 demonstrates yet another embodiment of the present invention. Baffle 16 is provided with a plurality of baffle legs 40. The baffle legs 40 can be adapted to cooperate with an intermediate piece 42. The intermediate piece 42 has a proximal and distal end such that various components can be attached to either or both ends. In this particular, exemplary, and non-limiting embodiment, intermediate piece 42 has an intermediate piece orifice 44 therethrough. This intermediate piece orifice 44 can be formed by one or more intermediate piece extensions 46. As with any orifice described herein, the size and shape of the orifice 44 may determine the potential back splash contamination and the interruption of the jet stream energy. Intermediate piece 42 can be connected to injector 18 and/or baffle 16 and/or insert 26 via an intermediate piece connector 48. The intermediate piece connector 48 can include any mechanism to attach one piece to another, and can further include a friction fit, bayonet, or screw fitting.

Therefore, as medication is extracted from the medication vial 50, it is drawn into the injector chamber 52 wherein the injection system 10 then delivers the medication through the injector canal 24, through the injector orifice 22, into the intermediate piece 42, through the intermediate piece orifice 44, and then through the various distal components.

As shown in FIG. 5, upon exiting the intermediate piece orifice 44, the medication will penetrate the protective layer 14 and then enter the baffle 16 via the baffle orifice 20, then through the insert reservoir 27, through the insert distal orifice 28, to then impact the skin 12.

Skin debris, if it has the correct trajectory, can enter the insert 26-baffle 16 component. Debris can either strike the baffle 16, such as baffle splash guards 54, or insert 26 itself, or can strike the protective layer distal surface 29. In the event that the debris has sufficient energy to re-puncture the layer 14, debris will then strike the intermediate piece 42, such as the intermediate piece extensions 46. In this manner, the only manner in which the injector tip is contaminated is if the debris enters the intermediate piece 42 at such a precise trajectory that is flies through the orifice 44 and directly hits the injector orifice 22.

However, although not shown in FIG. 5, a plurality of protective layers 14 can be used at various stages along the insert 26, baffle 26, or intermediate piece 42. Intermediate piece 42 can also include an optional intermediate piece channel 56, which fluidly communicates with the atmosphere and the intermediate piece lumen 57. This permits an equalization of pressure in the lumen 57 and also permits any debris in the lumen 57 to be evacuated. As for size, intermediate piece channel 56 can be approximately any size but may be about 1 mm.

Therefore, the injector assembly 10 provides increased resistance to contamination using a variety of components. It is noted that in any and all embodiments described herein, no individual component is critical or necessary for accomplishing the invention.

For example, the embodiment of FIG. 5 can be configured so that it does not have an insert 26, a baffle 16, a protective layer 16, or the intermediate piece 46. In FIG. 5, the addition of the insert 26 and baffle 16 provide added benefit.

Figure 6:
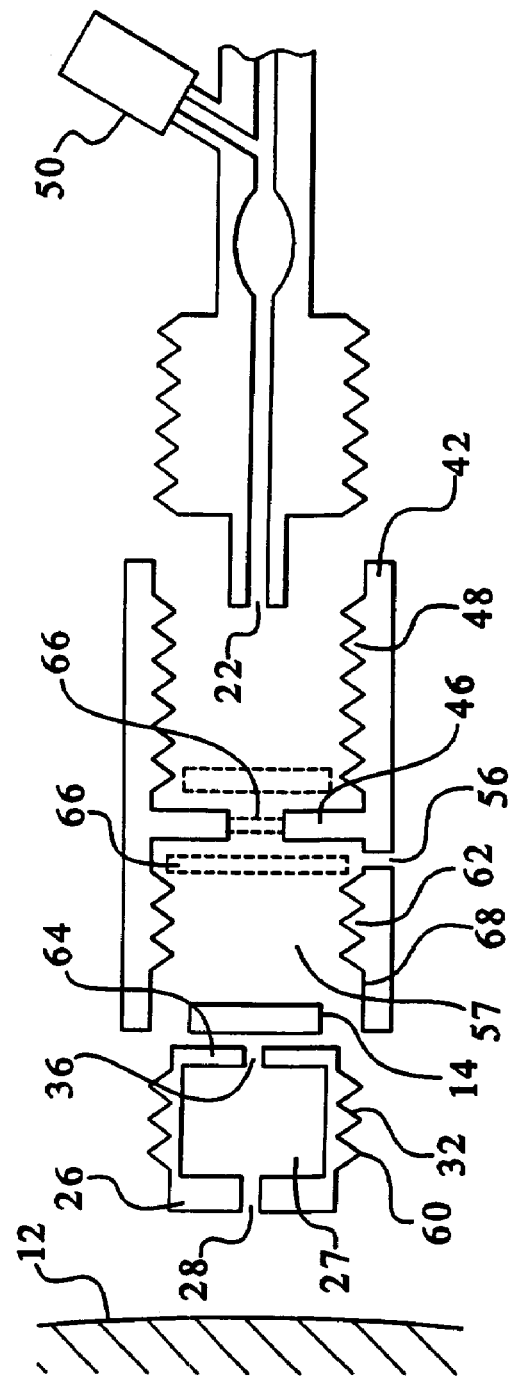
FIG. 6 shows yet another embodiment of the present invention in which a protective layer is shown at various positions.

FIG. 6 demonstrates yet another embodiment of the present invention. In this embodiment, an insert 26 plays many roles. First, the insert 26 is provided with an insert connector 60, shown here by example only, as a screw fitting. The intermediate piece 42 is provided with an intermediate piece distal connector 62, as shown by example only, as a screw fitting. Accordingly, the intermediate piece distal connector 62 cooperates with the insert connector 60 to provide a detachable attachment. The insert 26 is adapted to provide the same characteristics as the baffle 16 (not shown) in that it can be adapted to also have an insert splash guard 64. While the protective layer 14 is shown proximal to the insert 26, the intermediate piece 42 can also include an intermediate piece protective layer 66 located anywhere along the intermediate piece 42. This intermediate piece protective layer 66 is shown in phantom either distal to the intermediate piece orifice 44, coincident with the orifice 44, or proximal to the orifice 44. In this regard, the intermediate piece protective layer 66 is distal to the injector orifice 22. In operation, the debris that enters the insert 26 will likely impact the insert splash guard(s) 64, the protective layer 14, the intermediate piece extension(s) 46, or the intermediate piece protective layer 66. In this regard, the disposability of the components is enhanced in that the intermediate piece inner surface 68 remains generally clean in that most debris stays within the insert 26 or strikes the protective layers 14,66.

Figure 8:
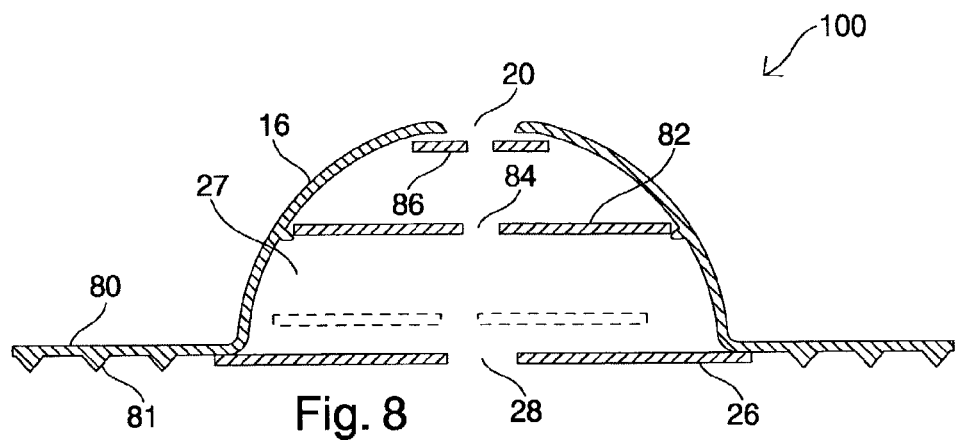
FIG. 8 is one embodiment of the protector cap of the present invention.

FIG. 8 depicts another embodiment of the present invention. The baffle 16 and the insert 26 may be heat-sealed or otherwise bonded to form an integral protector cap 100 with an insert reservoir 27. The baffle 16 may be a flat sheet or may have a dome shape, as depicted in FIG. 8 to facilitate intra-dermal injections, for example. In one embodiment, the baffle 16 and the insert 26 cannot be taken apart or modified without destroying the protector cap 100. The baffle 16 includes a flange 80 to which the insert 26 is bonded. In one embodiment, the baffle 16 may include ribs 81 on the flange 80 to stiffen the cap structure and ensure proper placement of the baffle layer against the skin and prevent slippage. The protective cap 100 may further include a disable device. In one embodiment, the disable device is a central washer 82 located between the baffle 16 and the insert 26 in the insert reservoir 27. The central washer 82 may also include a washer orifice 84 that lines up with the baffle orifice 20 and the insert orifice 28 when the central washer 82 is in an installed position. For use during an injection, the central washer 82 must be located in the installed position. Thus, the protector cap 100 creates four challenges for blood or debris to enter the injector canal 24: the insert orifice 28, the washer orifice 84, the baffle orifice 20, and the injector orifice 22.

Upon injection, the baffle 16 of the protector cap 100 becomes distorted due to the pressure created by the subject's skin 12 or by an injector component, as described below. The baffle 16 may also become distorted during packaging and shipping if not handled carefully. When the baffle 16 becomes distorted, the central washer 82 dislodges in the insert reservoir 27. As a result, the washer orifice 84 no longer lines up with the baffle orifice 20 and the insert orifice 28, thereby disabling the protector cap 100 for further use. As a result, entry of the debris or blood into the injector canal 24 is even more difficult because the orifices 28, 84, 20 and 22 are no longer aligned. In one embodiment, the central washer 82 is tinted to a different color than the insert 26 or baffle 16 so that the user can determine whether the central washer 82 is in the installed or disabled position.

Figure 9:
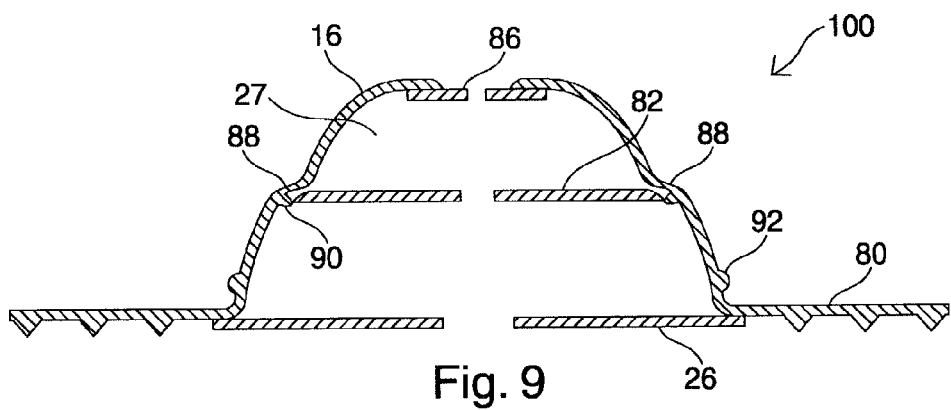
FIG. 9 is another embodiment of the protector cap of the present invention.
Figures 10A, 10B, 10C:
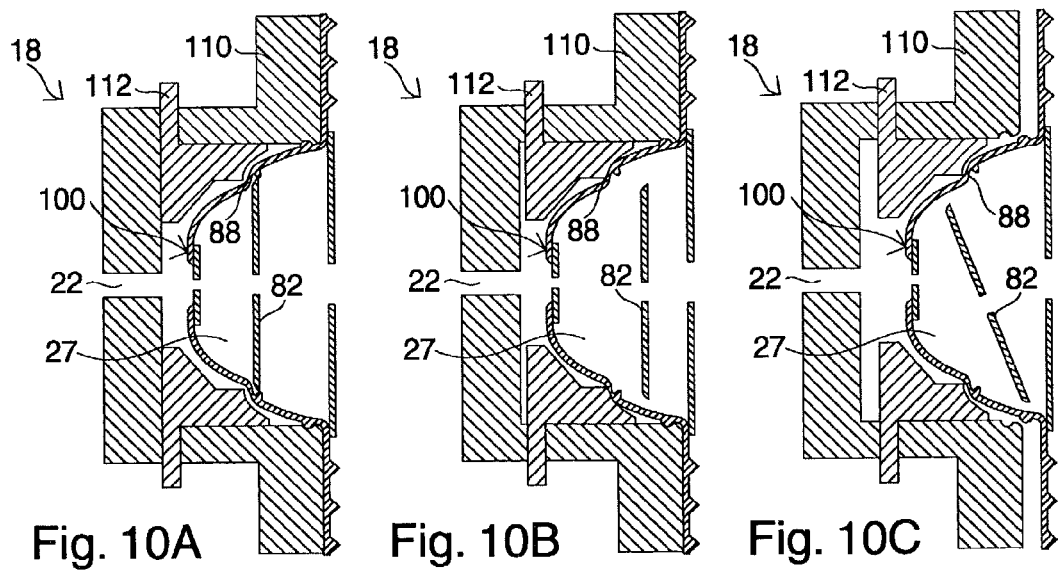
FIGS. 10A–C depict the operation sequence of the protector cap and injector during an injection.

In another embodiment of the protector cap 100 depicted in FIG. 9, the shape of the baffle 16 may be modified to ease the disabling of the protector cap 100. The insert 26 may include a hinge 88 having a lug 90 for holding the central washer 82 in the installed position. The hinge 88 produces a double hinge line that allows the baffle 16 to deflect as shown in the operation sequence of FIG. 10A–C. The hinge 88 provides for programmed deflection of the baffle 16 to ensure that the central washer 82 is dislodged before the cap 100 is ejected from the injector 18. Upon application of pressure, the baffle 16 distorts and pops the central washer 82 from its installed position on the lug 90 (FIG. 10A) to a dislodged position (FIG. 10B). In one embodiment, a bead 92 has been added near the flange 80 of the baffle 16. The bead 92 locks into a grove or other locking feature of a cap receiver 110 on the injector 18.

In the operation sequence of FIG. 10, pressure from the cap receiver 110 of the injector 18 distorts the baffle 16 rather than pressure from placement against the skin 12. A sliding sleeve 112 in the cap receiver 110 contacts the hinge 88 of the baffle 16, causing the hinge line of the hinge 88 to flex and knocking the central washer 82 out of its installed position. Once the central washer 82 is loose in the insert reservoir 27 of the protector cap 100, the protector cap 100 is disabled and will not allow a stream from the injector 18 to penetrate. After being disabled, the sliding sleeve 112 continues to move forward towards subject and pops the protector cap 100 free of the cap receiver 110. In one embodiment, the injector 18 cannot be fired unless the protector cap 100 is in the cap receiver 110.

The protector cap 100 may further include a protective layer 14, as described above. The protective layer 14 may cover the insert orifice 28, the washer orifice 84, the baffle orifice 20, or the injector orifice 22 or may be suspended within the insert reservoir 27. In another embodiment, the protector cap 100 may further include an upper washer 86 that holds the protective layer in place when the protective layer is made from a material that can not adhere to the material of the baffle 16.

Protector caps 100 may be packaged individually or in packets. In one embodiment, protector caps 100 are packaged as part of a kit. The protector caps 100 may be packaged in individual or numerous rows. A cradle with a separate well for each protector cap 100 may be sealed with an adhesive strip to provide a contamination free environment.

Figure 11:
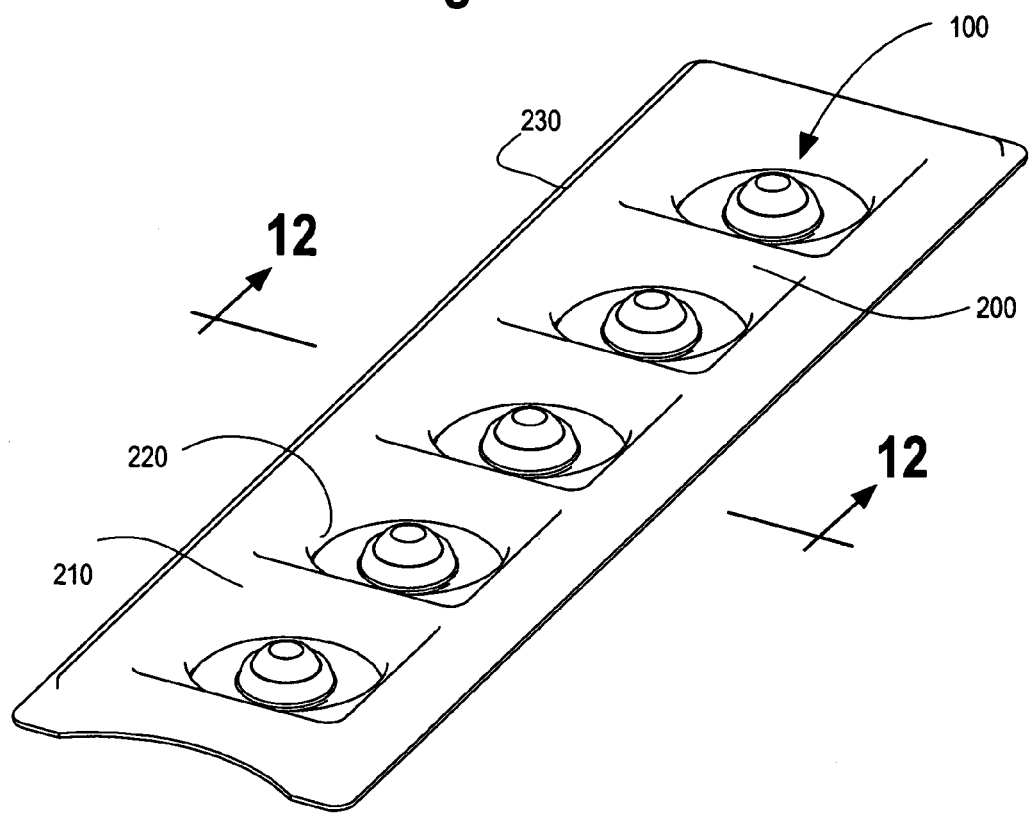
FIG. 11 shows an adhesive strip covering the cradle of a package for storing protector caps.
Figure 12:
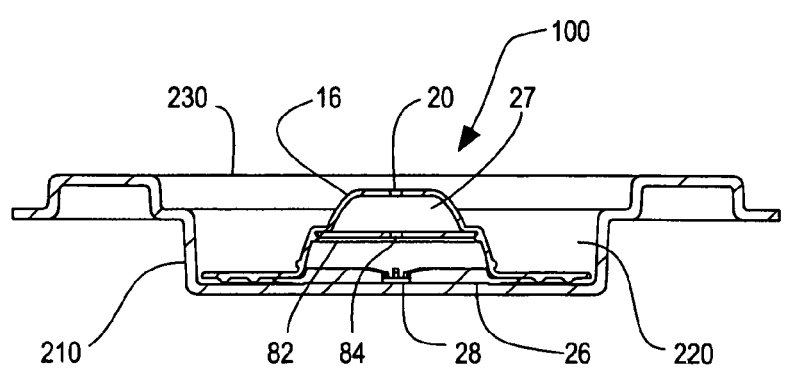
FIG. 12 is a sectional view of FIG. 11 along section line 12—12 showing a package for storing protector caps of the present invention and a protector cap.

FIG. 11 shows a package 200 for storing a plurality of protector caps 100. The package 200 has a cradle 210 having at least one row of separated wells 220 for storing one or more protector caps 100. The package 200 further includes an adhesive strip 230 covering the cradle 210 to preserve the hygienic nature of the protector caps 100 located in the wells 220 of the cradle 210 and to secure the protector caps 100 during shipping and transport. FIG. 12 is a sectional view of FIG. 11 taken along section line 12—12 shown in FIG. 11. FIG. 12 shows a protector cap 100 located in a well 220 of the cradle 210 of the package 200. Similar to the protector cap 100 illustrated in FIGS. 8, 9, bA, lOB and bC, the protector cap 100 shown in FIG. 12 has a baffle 16 which has a baffle orifice 20, a washer orifice 84 and an insert orifice 28 through which a medicament stream passes m order to accomplish a needle-free injection. Additionally, as previously explained, the presence of the baffle orifice 20, washer orifice 84 and an insert orifice 28 make it significantly more difficult for any resulting backsplash of biological debris from contaminating the injector. The protector cap 100 illustrated in FIG. 12 also has a central washer 82 with the washer orifice 84 passing therethrough. The central washer 82 is located in the insert reservoir 27 which is fonned by joining the insert 26 with the baffle 16 as previously described. FIG. 12 also shows a protector cap 100 located in a cradle 210, the adhesive strip 230 and the well 220 for storing the protector caps 100.

Although the present invention is described by reference to a single and exemplary embodiments, and the best mode contemplated for carrying out the present invention has been shown and described, it is to be understood that modifications or variations in the structure and arrangements of these embodiments other than those specifically set forth may be achieved by those skilled in the art and that such modifications are to be considered as being within the overall scope of the present invention. It is to be further understood that the following pending patent applications owned by the assignee of the instant application are hereby incorporated by reference in their entirety as if fully set forth herein: U.S. Ser. No. 09/685,499; PCT/US00/41122; U.S. Ser. No. 09/685,633; PCT/US00/27991; U.S. Ser. No. 09/717,548; PCT/US00/32186; U.S. Ser. No. 09/717,559; PCT/US00/32187; U.S. patent application Ser. No. 10/269,570 for "Jet Injector System with Hand Piece" filed on Oct. 11, 2002.

The invention claimed is:

1. An injection system, comprising: an injector having a distal end and a proximal end, wherein the injector comprises an injector orifice at the distal end; and a protector cap configured to cover the injector orifice at the distal end of the injector, wherein the protector cap comprises an insert having an insert orifice, a baffle having a baffle orifice, wherein the baffle is joined to the insert to form an insert reservoir, and a disable device located in the insert reservoir.

2. The injection system of claim 1, further comprising a protective layer located between the distal end of the injector and the protector cap.

3. The protector cap of claim 1, wherein the disable device has an installed position and a disabled position.

4. The protector cap of claim 3, wherein the disable device comprises a central washer having a washer orifice.

5. The injection system of claim 4, further comprising a protective layer covering at least one of the insert orifice, the washer orifice, and the baffle orifice.

6. A package for storing a plurality of protector caps comprising an insert having an insert orifice, a baffle having a baffle orifice, wherein the baffle is joined to the insert to form an insert reservoir, and a disable device located in the insert reservoir, comprising:

a cradle having at least one row of separated wells for storing the plurality of protector caps; and an adhesive strip covering the cradle.

7. A method of administering needle-free injections, comprising:

adapting an injector with a protector cap to minimize contamination of the injector; and administering a medication through the injector and the protector cap;

wherein the protector cap comprises an insert having an insert orifice, a baffle having a baffle orifice, wherein the baffle is joined to the insert to form an insert reservoir, and a disable device located in the insert reservoir.

8. The method of claim 7, wherein the step of administering a medication comprises administering a powder form of medicine.

9. The method of claim 7, wherein the step of administering a medication includes administering at least one of a DNA vaccine, a Hepatitis vaccine, a HIV vaccine, an anti-allergen, and a pharmaceutical.

10. A method of preventing back splash contamination of a needle-free injector, comprising:

adapting the injector with a protector cap to minimize contamination of the injector; and administering a medication through the injector and the protector cap;

wherein the protector cap comprises an insert having an insert orifice, a baffle having a baffle orifice, wherein the baffle is joined to the insert to form an insert reservoir, and a disable device located in the insert reservoir.

* * * * *